United States Patent [19]

Kleemann et al.

[11] 4,360,697

[45] Nov. 23, 1982

[54] PROCESS FOR THE PRODUCTION OF 1-AMINO-PROPANEDIOL-2,3

[75] Inventors: Axel Kleemann; Robert Nygren; Rudolf Wagner, all of Hanau, Fed. Rep. of Germany

[73] Assignee: Degussa Aktiengesellschaft, Frankfurt am Main, Fed. Rep. of Germany

[21] Appl. No.: 252,609

[22] Filed: Apr. 9, 1981

[30] Foreign Application Priority Data

Dec. 4, 1980 [DE] Fed. Rep. of Germany ....... 3014129

[51] Int. Cl.$^3$ ...................... C07C 89/02; C07C 91/10
[52] U.S. Cl. ..................................... 564/475; 564/507
[58] Field of Search ............................... 564/475, 477

[56] References Cited

U.S. PATENT DOCUMENTS 2,373,199  4/1945  Schwoegler et al. ............... 564/477
3,544,632  12/1970  Haarer ................................ 564/475

FOREIGN PATENT DOCUMENTS 544944   8/1957  Canada ................................. 564/475
1432428  2/1966  France ................................. 564/475
158167   1/1957  Sweden ................................ 564/475
760215   10/1956  United Kingdom ................ 564/475

OTHER PUBLICATIONS

Sidgwick, "The Organic Chemistry of Nitrogen," pp. 95 & 96, (1966).
Knorr, Berichte Deutsch. Chem. Ges. vol. 32, pp. 750-757, (1899).
Baum, J. Org. Chem. vol. 27, pp. 2231-2233, (1962).

*Primary Examiner*—John Doll
*Attorney, Agent, or Firm*—Cushman, Darby & Cushman

[57] ABSTRACT

The production of 1-amino-propanediol-2,3 is attained with good yields and in an industrially simple manner by reacting liquid ammonia with glycidol under pressure in the presence of a small amount of an organic solvent.

42 Claims, No Drawings

PROCESS FOR THE PRODUCTION OF 1-AMINO-PROPANEDIOL-2,3

BACKGROUND OF THE INVENTION

The production of 1-amino-propanediol-2,3 by the addition of ammonia to glycidol (glycidol) was first described by L. Knorr and E. Knorr (Ber. deutsch. Chem. Ges. vol. 32, pages 750–757 (1899)). The authors employed thereby one part by weight of glycidol with 100 parts by weight of 25% aqueous ammonia and then obtained after working up by distillation 1-amino-propanediol-2,3 in a yield of 44% based on the glycidol employed. The weight ratio of glycidol to aqueous ammonia (25%)=1:100 means a mole ratio of glycidol to ammonia=1:109.

This method of production of 1-amino-propanediol-2,3 was examined by K. Baum and W. T. Maurice (J. Org. Chem. Vol. 27, pages 2231–2233 (1962), in which case under the same conditions they obtained a yield of 68% of theory. This better yield is based on the fact that the first mentioned authors distilled the reaction product at 235°–250° C./320 mmHg, while the last mentioned authors carefully distilled, namely at 80°–106° C./0.1–0.15 mmHg and therewith did not cause loss through thermal decomposition.

While the last named process also brings about better yields compared to the process of Knorr (loc. cit.), the amounts of aqueous ammonia supplied to the cycle represents a considerable load in the industrial carrying out of the process.

Besides, it requires a very large reaction space because of the above-mentioned molar ratio of glycidol to ammonia, as well as a distillation plant for the concentration of the diluted aqueous ammonia solution supplied to the cycle.

The object of the invention, therefore, is the development of a process for the production of 1-amino-propanediol-2,3 in good yields and in an industrially simple manner.

SUMMARY OF THE INVENTION

It has now been found that the reaction of glycidol with ammonia in homogeneous liquid phase with good yields and without particular industrial expense can be carried out if glycidol and liquid ammonia are reacted together under such pressure that the ammonia remains liquid in the presence of a small amount of an organic solvent miscible with liquid ammonia.

As organic solvent miscible with ammonia there are suited hydrocarbons, above all aromatic hydrocarbons, as well as lower primary or secondary alcohols, especially aliphatic alcohols, e.g. alkanols as well as glycol ethers.

Especially suited are alkylated benzenes such as toluene as well as methanol, ethanol, propanol-1 and propanol-2. Other solvents which can be used include benzene, xylene (any of the isomers or mixtures thereof), ethyl benzene, 1,4-dioxane, tetrahydrofuran, ethylene glycol mono methyl ether, ethylene glycol dimethyl ether, butanol-1, butanol-2, 2-methyl-butanol-1, ligroin, decane, octane.

In general, the molar ratio of glycide to liquid ammonia is in the range of 1:5 to 20.

Preferably, there is a molar ratio 1:10 to 20.

The expression "small amount of an organic solvent" is in relation to the very large amounts of recycling water in the state of the art (loc. cit.)

In the present process there are needed substantially smaller amounts of an organic solvent. Thus, the weight ratio of glycidol to the organic solvent is in the range of 1:0.2 to 1:10, preferably the range is 1:1.

The pressure range is between 5 and 150 bar, preferably 20 to 90 bar.

As reaction temperature there is used 20° to 180° C., preferably 50°–120° C.

Temperatures above and below the range mentioned are possible but lead at temperatures below the mentioned range to undesirably long reaction time and at those above the range to greatly increased formation of byproducts.

The industrial advantage of the process of the invention, which can be carried out either discontinuously (batchwise) or continuously, is in the substantially increased space-time yields compared to the state of the art, namely around a factor of 50 compound to the process of Baum and Maurice (loc. cit.)

Besides the process operates with greatly reduced amounts of liquid so that the recycling is simplified.

It could not be foreseen that this industrial advance was possible merely by the presence of a comparatively small amount of an organic solvent.

Unless otherwise indicated, all parts and percentages are by weight.

The process can comprise, consist essentially of, or consist of the steps set forth with the stated materials.

The invention will be explained in more detail in connection with the following examples.

DETAILED DESCRIPTION

Experimental Apparatus

The following examples were carried out in the following experimental apparatus.

By means of two pumps, regulated amounts of the reactants were conveyed into the reactor from a supply reservoir filled with glycidol or glycidol/organic solvent and a pressure flask containing liquid ammonia. This consisted of a double walled tube wherein the outer jacket space serves, with the help of water, to bring the reaction mixture in the inner tube to the desired temperature and to carry off the heat of reaction. The reaction was carried out in liquid, homogeneous phase. The pressure needed to liquify the reaction was held through a pressure control valve at the end of the double jacketed tube. The inner tube, thus the reaction zone, had a volume of 4.2 liters. After passing through the reaction zone, the reaction mixture was relieved of pressure at the pressure control valve and led into a reservoir. Hereby, there escaped from the crude product up to over 99% of the ammonia employed in excess, which after condensation, could again be supplied to the reaction. From the crude product, the 1-amino-propanediol-2,3 was recovered by fractional vacuum distillation.

EXAMPLE 1

There were dosed into the above-mentioned reactor at 85° C. and 43 bar per hour 0.5 kg of glycidol, 0.5 kg of toluene and 1.7 kg of liquid ammonia. (Molar ratio glycidol:ammonia=1:16.8, weight ratio of glycidol to toluene=1:1). After working up the reaction product by distillation, there were obtained 0.33 kg of aminopropanediol per hour, corresponding to 53.5% of theory, based on the glycidol employed. Boiling point: 94° C. (0.2 Torr), purity=99.5% (amine titration).

EXAMPLE 2

There were dosed into the above-mentioned reactor at 85° C. and 43 bar per hour 0.6 kg of glycidol, 0.6 kg of propanol-2 and 1.25 kg of liquid ammonia (Molar ratio glycidol:ammonia=1:16, weight ratio of glycidol to propanol-2=1:1). After working up the reaction product by distillation, there were obtained 0.43 kg of aminopropanediol per hour, corresponding to 58.2% of theory, based on the glycidol employed.

EXAMPLE 3

There were dosed into the above-mentioned reactor at 85° C. and 43 bar per hour 0.7 kg of glycidol, 0.7 kg of propanol-2 and 1.6 kg of liquid ammonia. (Molar ratio glycidol:ammonia=1:10, weight ratio of glycidol to propanol-2=1:1). After working up the reaction product by distillation, there were obtained per hour 0.4 kg of aminopropanediol, corresponding to 54.3% of theory, based on the glycidol employed.

EXAMPLE 4

There were dosed into the above-mentioned reactor at 85° C. and 43 bar per hour 0.6 kg of glycidol, 0.6 kg of 1,4-dioxane and 2.1 kg of liquid ammonia. (Molar ratio glycidol:ammonia=1:16, weight ratio of glycidol to 1,4-dioxane=1:1). After working up the reaction production by distillation, there was obtained 0.4 kg of aminopropanediol per hour, corresponding to 54.2% of theory, based on the glycidol employed.

In Examples 2–4 also the boiling point and the purity of the product correspond to the data given in Example 1.

The entire disclosure of German priority application P 3014129.8 is hereby incorporated by reference.

What is claimed is:

1. In a process for the production of 1-aminopropanediol-2,3 by the reaction of glycidol with ammonia the improvement comprising reacting glycidol and liquid ammonia under pressure sufficient to keep the ammonia in liquid form in the presence of an organic solvent miscible with liquid ammonia.
2. A process according to claim 1 wherein the glycidol and liquid ammonia are employed in a molar ratio of 1:5 to 20.
3. A process according to claim 1 wherein the glycidol and liquid ammonia are employed in a molar ratio of 1:10 to 1:20.
4. A process according to claim 1 wherein the solvent is a hydrocarbon, a lower primary or secondary alcohol or a glycol ether.
5. A process according to claim 4 wherein the solvent is an alkylated benzene.
6. A process according to claim 5 wherein the solvent is toluene.
7. A process according to claim 4 wherein the solvent is lower alkanol.
8. A process according to claim 7 wherein the solvent is methanol, ethanol, propanol-1 or propanol-2.
9. A process according to claim 8 wherein the solvent is propanol-2.
10. A process according to claim 4 wherein the solvent is a glycol ether.
11. A process according to claim 10 wherein the ether is 1,4-dioxane or tetrahydrofuran.
12. A process according to claim 11 wherein the solvent is 1,4-dioxane.
13. A process according to claim 2 wherein the solvent is a hydrocarbon, a lower primary or secondary alcohol or a glycol ether.
14. A process according to claim 13 wherein the solvent is an alkylated benzene, a lower alkanol, 1,4-dioxane or tetrahydrofuran.
15. A process according to claim 1 wherein the weight ratio of glycidol to organic solvent is from 1:0.2 to 1:10.
16. A process according to claim 2 wherein the weight ratio of glycidol to organic solvent is from 1:0.2 to 1:10.
17. A process according to claim 16 wherein the solvent is a hydrocarbon, a lower primary or secondary alcohol or a glycol ether.
18. A process according to claim 17 wherein the solvent is an alkylated benzene, a lower alkanol, 1,4-dioxane or tetrahydrofuran.
19. A process according to claim 15 wherein the weight ratio of glycidol to organic solvent is 1:1.
20. A process according to claim 16 wherein the weight ratio of glycidol to organic solvent is 1:1.
21. A process according to claim 17 wherein the weight ratio of glycidol to organic solvent is 1:1.
22. A process according to claim 18 wherein the weight ratio of glycidol to organic solvent is 1:1.
23. A process according to claim 1 wherein the reaction is carried out at a pressure of 5 to 150 bar.
24. A process according to claim 18 wherein the reaction is carried out a pressure of 5 to 150 bar.
25. A process according to claim 1 wherein the reaction is carried out at a pressure of 20 to 90 bar.
26. A process according to claim 22 wherein the reaction is carried out at a pressure of 20 to 90 bar.
27. A process according to claim 21 wherein the reaction is carried out at a pressure of 20 to 90 bar.
28. A process according to claim 20 wherein the reaction is carried out at a pressure of 20 to 90 bar.
29. A process according to claim 19 wherein the reactin is carried out at a pressure of 20 to 90 bar.
30. A process according to claim 18 wherein the reaction is carried out at a pressure of 20 to 90 bar.
31. A process according to claim 17 wherein the reaction is carried out at a pressure of 20 to 90 bar.
32. A process according to claim 16 wherein the reaction is carried out at a pressure of 20 to 90 bar.
33. A process according to claim 15 wherein the reaction is carried out at a pressure of 20 to 90 bar.
34. A process according to claim 33 wherein the temperature is 50° to 120° C.
35. A process according to claim 1 wherein the materials employed consist essentially of glycidol, the inorganic solvent and liquid ammonia.
36. A process according to claim 1 wherein the materials employed consist of glycidol, the inorganic solvent and liquid ammonia.
37. A process according to claim 36 wherein the glycidol and liquid ammonia are employed in a molar ratio of 1:5 to 1:20, the pressure is 5 to 150 bar, the temperature is 50° to 120° C. and the weight ratio of glycidol to organic solvent is from 1:0.2 to 1:10.
38. A process according to claim 37 wherein the organic solvent is a lower alkanol.
39. A process according to claim 37 wherein the solvent is a hydrocarbon.
40. A process according to claim 39 wherein the hydrocarbon is an alkylated benzene.
41. A process according to claim 37 wherein the organic solvent is a glycol ether.
42. A process according to claim 41 wherein the glycol ether is 1,4-dioxane or tetrahydrofuran.

* * * * *